United States Patent
Albrecht et al.

(10) Patent No.: US 9,409,037 B2
(45) Date of Patent: Aug. 9, 2016

(54) ENHANCED ANTI-MICROBIAL PDT (75) Inventors: Volker Albrecht, Nuthetal (DE); Gerhard Wieland, Jena (DE); Burkhard Gitter, Jena (DE); Wolfgang Neuberger, Dubai (AE)

(73) Assignee: Biolitec Pharma Marketing LTD, Labuan (MY)

( * ) Notice: Subject to any disclaimer, the term of this patent is extended or adjusted under 35 U.S.C. 154(b) by 61 days.

(21) Appl. No.: 13/006,274

(22) Filed: Jan. 13, 2011

(65) Prior Publication Data

US 2011/0178580 A1 Jul. 21, 2011

Related U.S. Application Data (60) Provisional application No. 61/296,084, filed on Jan. 19, 2010.

(51) Int. Cl.
- *A61N 5/06* (2006.01)
- *A61M 1/36* (2006.01)
- *A61L 2/00* (2006.01)

(52) U.S. Cl.
CPC .............. *A61N 5/062* (2013.01); *A61L 2/0029* (2013.01); *A61L 2/0052* (2013.01); *A61M 1/3681* (2013.01); *A61N 5/0624* (2013.01); *A61L 2202/21* (2013.01); *A61M 1/3686* (2014.02); *A61N 2005/063* (2013.01); *A61N 2005/0652* (2013.01)

(58) Field of Classification Search
CPC .......... A61M 1/16; A61M 1/34; A61M 1/36; A61M 1/3472; A61M 1/3681; A61L 2/0029; A61L 2/0052; A61N 5/062

USPC ......... 607/88; 606/4.01, 5.01; 604/4.01, 5.01, 604/6.04, 6.08, 6.09

See application file for complete search history.

(56) References Cited

U.S. PATENT DOCUMENTS

| | | | | |
|---|---|---|---|---|
| 4,573,962 A | * | 3/1986 | Troutner | 604/6.08 |
| 5,171,749 A | * | 12/1992 | Levy | A61K 49/0036 514/3.7 |
| 5,912,257 A | * | 6/1999 | Prasad et al. | 514/356 |
| 6,277,337 B1 | * | 8/2001 | Goodrich et al. | 422/186.3 |
| 6,969,367 B2 | * | 11/2005 | Tu et al. | 604/6.04 |
| 7,470,245 B2 | * | 12/2008 | Tu et al. | 604/6.09 |

(Continued)

*Primary Examiner* — William Thomson
*Assistant Examiner* — Nathan J Jenness
(74) *Attorney, Agent, or Firm* — BJ Associates; Bolesh J. Skutnik

(57) ABSTRACT

Methods and devices to eliminate, reduce, destroy and/or inhibit undesired body fluid species, such as pathogen microbes and deteriorated or malignant cells in complex environments like blood, serum and other body fluids are provided. In preferred embodiments, an antimicrobial photodynamic therapy (PDT) treatment is given that effectively inactivates, reduces and/or destroys both Gram (−) and Gram (+) bacteria in complex body fluids. Methods to enhance antimicrobial PDT activity include administering a photosensitizer to bacteria-contaminated fluid, after a dwell time guiding bacteria-contaminated fluid with photosensitizer through a channel, emitting radiation preferably in an intermittent manner, and restoring treated body fluids to corresponding body regions. Electromagnetic radiation is preferably delivered intermittently with pulse width based on treatment parameters. Additionally, the method/device diminishes adverse host's inflammatory responses by neutralizing the biological activity of pathogenic microorganism fragments and reducing and/or removing pathogenic microorganism fragments responsible for it.

10 Claims, 5 Drawing Sheets

(56) References Cited

U.S. PATENT DOCUMENTS

| | | | |
|---|---|---|---|
| 2002/0015662 A1* | 2/2002 | Hlavinka | 422/24 |
| 2003/0060747 A1* | 3/2003 | Fries et al. | 604/6.08 |
| 2004/0256329 A1* | 12/2004 | Meserol et al. | 210/748 |
| 2005/0049228 A1* | 3/2005 | Albrecht et al. | 514/150 |
| 2007/0178436 A1* | 8/2007 | Wu | A61L 2/0011 435/2 |

* cited by examiner

ENHANCED ANTI-MICROBIAL PDT

DOMESTIC PRIORITY UNDER 35 USC 119(e)

This application claims the benefit and priority of U.S. Provisional Application Ser. No. 61/296,084 filed Jan. 19, 2010, entitled "Enhanced Anti-Microbial PDT" by Volker Albrecht, Gerhard Wieland, Burkhard Gitter and Wolfgang Neuberger, which is incorporated by reference herein.

BACKGROUND OF THE INVENTION

1. Field of the Invention

The invention relates to the field of novel therapies aimed to eliminate, kill or inhibit undesired body fluid species, such as pathogen microbes responsible for human and animal infections. More particularly the invention relates to an enhanced photodynamic therapy capable of eliminating or destroying undesired body fluid species, such as bacteria, in complex environment like whole blood, blood serum and other human and animal body fluids.

2. Invention Disclosure Statement

Photodynamic therapy (PDT) has emerged as a promising treatment of cancer and other diseases utilizing activation of an external chemical agent called photosensitizer or PDT drug, by light. Photosensitizers are administered systemically, locally or topically. After a determined period of time after being administered, the photosensitizer is preferentially retained by the tissue to be treated as compared to its concentration on healthy cells. Subsequently light of specific wavelength is delivered to the site to be treated. The PDT drug absorbs the light, rises to an excited state and then reacts with local oxygen producing reactive oxygen species that can destroy the cells which have retained a high concentration of photosensitizer, with minimal damage to surrounding healthy cells. Moreover, PDT has the advantage of dual selectivity, in that a photosensitizer can be targeted to its destination cell or tissue and, in addition, the illumination can be spatially directed to the lesion destination too.

While PDT has been shown to be an effective therapy regarding its selectivity and efficiency to treat cancer cells it has also been shown to be useful in treating infectious diseases caused by many but not all pathogen bacteria. Moreover, with the recent number of reports about bacterial strains becoming resistant to frequent doses of antibiotics, PDT appears to be an attractive alternative to conventional antibacterial methods.

Regardless of its potential as a promising therapy, there are still some issues to be solved concerning its antimicrobial effectiveness in different body fluids. Antibacterial PDT has been demonstrated to work well in aqueous environments, while in blood serum its effectiveness is diminished. Moreover, it has been found that bacterial cells in complex media (e.g. whole blood, plasma, blood serum) are much less susceptible to standard photosensitizers due to the blocking action of the components of the blood, such as albumin, whose presence decreases the activity of photosensitizers. It is speculated that albumin present in blood serum competes with bacteria by its adhesion to typical photosensitizers and captures a disproportionate amount at higher serum concentrations rendering typical PDT treatments ineffective. Whereas some photosensitizers can provide sufficient killing rates at half blood serum concentration, efforts to kill bacteria effectively in an environment saturated with blood serum are usually frustrated. In consequence, a method capable of dealing with the competition effect between blood serum components and typical photosensitizer compounds would be advantageous in order to enhance PDT treatments.

Additionally, none of the known photosensitizers and their conjugates is effective against all bacteria, as activity remains somewhat dependent on the chemical structure of the photosensitizers. Furthermore, Gram (−) bacterial cells have generally been the hardest to inactivate due to their protective double-layer outer membrane, making them resistant to many antimicrobial therapies.

In an attempt to effectively destroy bacteria, including Gram (+) and (−) bacteria, in complex media, such as blood serum, Patent Publications WO/2005/021094 and US 2005/0049228 disclose a method and composition utilizing Safranin O, a red dye that absorbs in the 450-600 nm, and electromagnetic radiation. While it successfully addresses a very good killing in the case of Gram (+) bacteria and sufficient killing of some Gram (−) bacteria in complex media, it would be desirable to obtain a more efficient destroying and killing effect in complex media than available in the prior art.

Once again, aiming to have a broad-spectrum antimicrobial activity in PDT therapy, Patent Application WO2006/093891A2 discloses a method for providing antimicrobial therapy and photosensitizer compounds for PDT, based on functionalized fullerene molecules. The method includes directing light onto the administered fullerene species to produce cytotoxic species and kill microbial cells. Even though the invention copes with killing both Gram (−) and Gram (+) bacteria, it has proved to be effective only in PBS and serum, and there is no mention about fullerene photosensitizer compound effectiveness in an environment saturated with blood serum, human plasma or human blood. These complex body fluids have proteins that are more likely to bind the photosensitizer, thus diminishing the actual concentration available to bind to bacteria.

Thus, there is a need to enhance the effectiveness of prior art antimicrobial PDT treatments, aiming to kill, destroy or inactivate a wide variety of microbes causing infectious diseases, including the more resistant Gram (−) bacterial cells, in saturated blood serum, whole blood and other complex body fluids, commonly present in real patient treatment settings.

OBJECTIVES AND BRIEF SUMMARY OF THE INVENTION

It is an objective of the present invention to provide a method to effectively reduce, eliminate, destroy and/or inactivate undesired body fluid species, such as deteriorated or malignant cells and/or pathogenic microorganisms causing infectious diseases.

It is another objective of the present invention to provide a device for partial or complete reduction, elimination, destruction and/or inactivation of undesired body fluid species, such as deteriorated or malignant cells and/or pathogenic microorganisms causing infectious diseases.

It is still another objective of the present invention to provide an enhanced antimicrobial PDT method for inactivation, reduction and/or destruction of both Gram (−) and Gram (+) bacteria.

It is still another objective of the present invention to provide an enhanced PDT method for elimination, inactivation, reduction and/or destruction of deteriorated and/or malignant cells in complex environments like whole blood, blood serum and other body fluids.

It is yet another objective of the present invention to provide an enhanced antimicrobial PDT method for inactivation, reduction and/or destruction of bacteria in complex environments like whole blood, blood serum and other body fluids.

It is a further objective to provide an improved PDT device capable of emitting electromagnetic radiation, with continuous or intermittent delivery of light, in order to sequentially activate the photosensitizer added to the body fluid to be treated, to partially or completely reduce, eliminate, destroy and/or inactivate undesired body fluid species.

It is a further objective of present invention to provide a method and device for neutralizing and/or inactivating the biological activity of pathogenic microorganism fragments and reducing and/or removing pathogenic microorganism fragments which can cause a host's inflammatory response such as systemic inflammatory response syndrome (SIRS), sepsis, severe sepsis and septic shock.

Briefly stated, the invention provides enhanced methods and improved devices to eliminate, reduce, destroy and/or inhibit undesired body fluid species, such as pathogen microbes and deteriorated or malignant cells in complex environments like blood, serum and other body fluids. In preferred embodiments, present invention provides an antimicrobial PDT treatment that effectively inactivates, reduces and/or destroys both Gram (−) and Gram (+) bacteria in complex body fluids. Methods to enhance antimicrobial PDT activity includes the steps of administering a photosensitizer to bacteria-contaminated fluid, after a dwell time guiding bacteria-contaminated fluid with photosensitizer through a channel, emitting radiation preferably in an intermittent manner, and restoring treated body fluids to corresponding body regions. Electromagnetic radiation is preferably delivered intermittently with pulse width based on treatment parameters. Preferred device embodiments comprise guiding channels and at least one electromagnetic radiation source, arranged separately or in sequence. Preferably, laser device or LED-panels are used to deliver electromagnetic radiation to activate the photosensitizer. When used with preferred photosensitizer composition based on Safranin O, preferred laser radiation wavelength is in the range of 500-580 nm. Additionally, present invention diminishes adverse host's inflammatory responses by neutralizing the biological activity of pathogenic microorganism fragments and reducing and/or removing pathogenic microorganism fragments responsible for it.

The above and other objects, features and advantages of the present invention will become apparent from the following description read in conjunction with the accompanying drawings.

DETAILED DESCRIPTION OF PREFERRED EMBODIMENTS

The present invention provides devices and methods to improve antimicrobial PDT therapies and enhance PDT elimination, reduction and/or inactivation of undesired body fluid species by effectively illuminating the detrimental bacteria, pathogen microorganisms and deteriorated or malignant cells. The devices and methods provided by the present invention enhance prior art antimicrobial PDT therapies as they can effectively kill, reduce and/or destroy microbes in blood serum, whole blood, and other complex body fluids. "Complex body fluids" include without limitation whole blood, blood serum, blood products, saliva, serum, lymph, amniotic fluid, aqueous humor, urine, cerebrospinal fluid, and other known body fluids. "Blood products" comprises human fresh frozen plasma, thrombocyte concentrates, red blood cells (RBC), blood clotting factors (V, VII, IX, X and XIII) and similar.

Furthermore, the microbes that may be killed, reduced, and/or destroyed include viruses and resistant Gram (−) and Gram (+) bacteria. Moreover, due to the effectiveness of the present invention as enhanced antimicrobial PDT treatment, the invention offers an advantageous therapy to treat a leading cause of mortality and morbidity among ill patients: sepsis. As this disease is characterized by an extended blood infection produced by pathogenic microorganism fragments the present invention provides a more effective treatment unattainable at present.

To effectively kill, reduce and/or destroy undesired body fluid species in complex body fluids like diluted or undiluted serum or solutions containing blood or blood compounds, a preferred embodiment consists of a device for enhanced photodynamic therapy comprising at least one channel for complex body fluids and at least one electromagnetic radiation source. Preferably, a portion of the channel through which complex body fluids flow has a cylindrical or helical shape, with one or more sections of said channel made with a material which allows partial or total electromagnetic radiation transmission. Preferably, the electromagnetic radiation source can be a coherent or incoherent radiation source selected from the group of laser radiation sources, light emitting diode sources, lamp radiation sources and combinations of them. In order to be used for photodynamic therapy, the electromagnetic radiation source emits at least one electromagnetic radiation of a wavelength that activates or is absorbed by at least one exogenously administered photosensitizer or photosensitizer precursor. In a preferred embodiment, at least one electromagnetic radiation source emits an electromagnetic radiation wavelength preselected from a range of about 500 nm and 580 nm. In another embodiment, electromagnetic radiation energy can be delivered with the aid of a waveguide selected from the group of optical fibers, arrays of optical fibers, optical fibers with cylindrical diffuser tips, and combinations of them.

Figure 1:
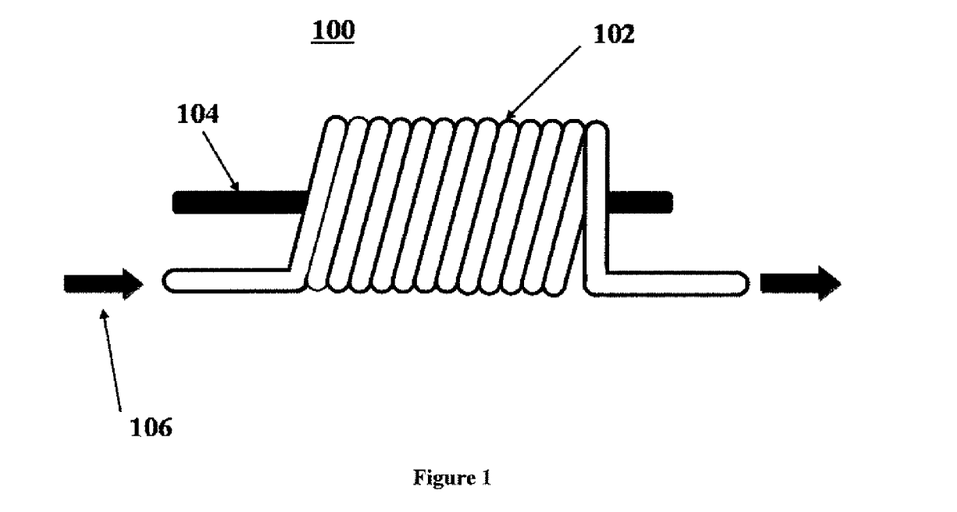
FIG. 1 depicts an embodiment of the present invention, showing an antimicrobial PDT device to enhance microbial killing effect against bacteria, such as Gram (−) and Gram (+) bacteria in complex body fluids.

One preferred embodiment includes device 100 shown in FIG. 1 to effectively kill, reduce and/or destroy undesired body fluid species, such as Gram (−) and Gram (+) bacteria in complex body fluids, which comprises helical channel 102 and cylindrical diffuser 104, capable of emitting electromagnetic radiation, preferably laser radiation. Cylindrical diffuser's 104 axis passes through the internal axis of helical channel 102. After a dwell time from the administration of a photosensitizer or photosensitizer precursor, contaminated medium 106, such as bacteria-contaminated human plasma, flows through helical channel 102 while cylindrical diffuser 104 emits electromagnetic radiation tuned to the activation wavelength of the selected photosensitizer. The photosensitizer or photosensitizer precursor may be activated by any electromagnetic radiation source including coherent and incoherent radiation sources such as laser radiation source, light emitting diodes source and lamp radiation source (including, incandescent, xenon arc and metal halide lamps). Electromagnetic radiation may be delivered through lamps and waveguides such as optical fibers with or without diffuser tips. In this embodiment laser radiation is preferred and may be delivered with the aid of optical fiber apparatus or arrays, containing diffusers or other devices as needed, preferably optical fibers with cylindrical diffuser tips. In order to enhance antibacterial PDT treatment, laser radiation is preferably emitted intermittently while contaminated medium 106 flows through helical channel 102.

Figure 2:
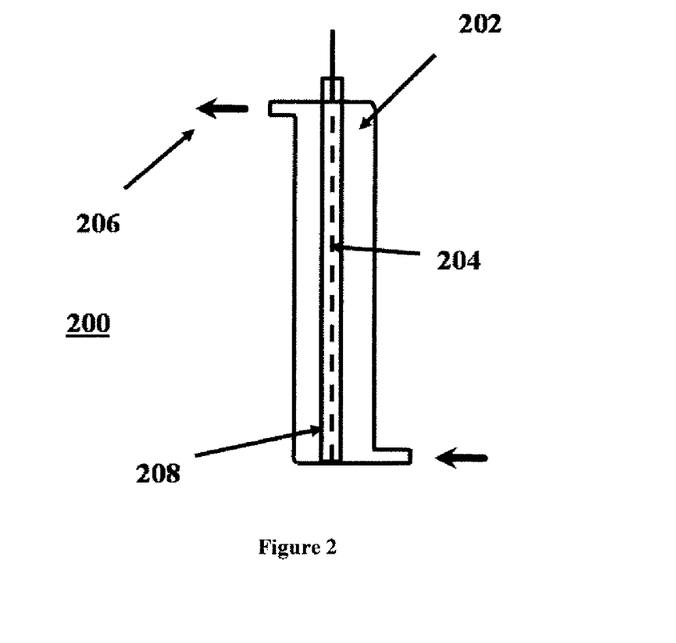
FIG. 2 shows another embodiment of the present invention depicting a device to perform antimicrobial PDT against microbes, such as Gram (−) and Gram (+) bacteria in complex body fluids.

In another preferred embodiment, device 200 depicted in FIG. 2 comprises external cylindrical channel 202 and internal channel 208 containing cylindrical diffuser 204 capable of emitting laser radiation. Initially, photosensitizer is administrated to the infected subject and following a dwell period of time, contaminated medium 206 flows around internal channel 208 while cylindrical diffuser 204 emits laser radiation, tuned to the activation wavelength of the selected photosensitizer. Preferably laser radiation is emitted intermittently while contaminated medium 206 flows through cylindrical channel 202. Preferably, external cylindrical channel 202 and internal channel 208 containing cylindrical diffuser 204 are made of glass, but not limited thereto. External cylindrical channel 202 has a diameter between 5 and 50 mm, preferably between 10 and 15 mm and length in the range of 30 to 300 mm, preferably between 90 and 110 mm. Internal channel 208 containing cylindrical diffuser 204 has an inner diameter between 0.5-5 mm, preferably between 1.5-2 mm. Nonetheless precise dimensions of external cylindrical channel 202 and internal channel 208 will be determined depending on desired flow parameters of contaminated medium 206 while passing through external cylindrical channel 202 and desired effect while performing antimicrobial PDT therapy. Once again the present embodiment allows an effective antimicrobial activity, killing, reducing and/or destroying undesired body fluid species, such as Gram (−) and Gram (+) bacteria in complex body fluids.

Figure 3A:
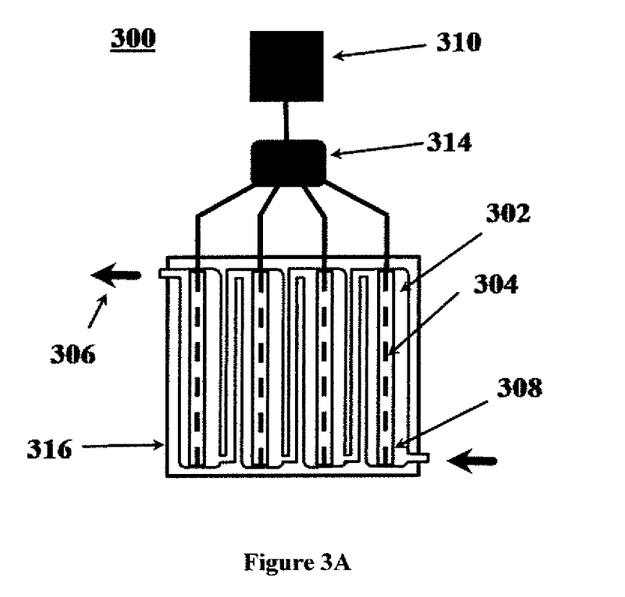
FIG. 3A presents a preferred embodiment depicting a laser device to perform PDT therapy aiming to partially or completely eliminate undesired body fluid species in complex body fluids.
Figure 3B:
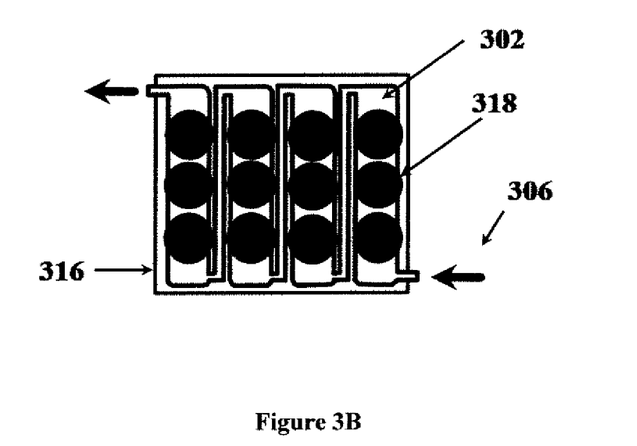
FIG. 3B shows another preferred embodiment depicting LED panel device to perform PDT therapy aiming to partially or completely eliminate undesired body fluid species in complex body fluids.

Another preferred embodiment is illumination unit/device 300 depicted in FIGS. 3A and 3B. FIG. 3A shows an embodiment consisting of a number of external cylindrical channels 302, similar to the one exemplified in previous embodiment, connected to each other in a way that allows contaminated medium 306 to flow sequentially through all of them. Each cylindrical channel 302 holds inside cylindrical diffuser 304 and internal channel 308. The array of external cylindrical channels 302 is enclosed in case 316 equipped with a cooling system. When contaminated medium 306 containing photosensitizer is directed through the array of external cylindrical channels 302, laser device 310 is activated, emitting laser radiation intermittently in a preselected pattern. Between laser device 310 and external cylindrical channel 302 there is beam-splitter 314 that directs laser radiation to each cylindrical channel 302. FIG. 3B shows another preferred embodiment in which LED-panels 318 emit radiation to activate the photosensitizer added to contaminated medium 306 that flows through the array of cylindrical channels 302. LED-panels 318 and the array of cylindrical channels 302 are enclosed in case 316 equipped with a cooling system.

Figure 4A:
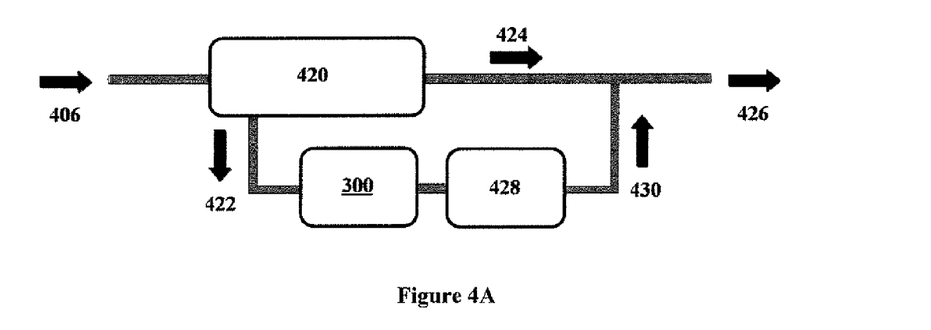
FIG. 4A illustrates a preferred embodiment showing device for enhanced antimicrobial PDT treatment coupled to continuous plasma filtration adsorption therapy.
Figure 4B:
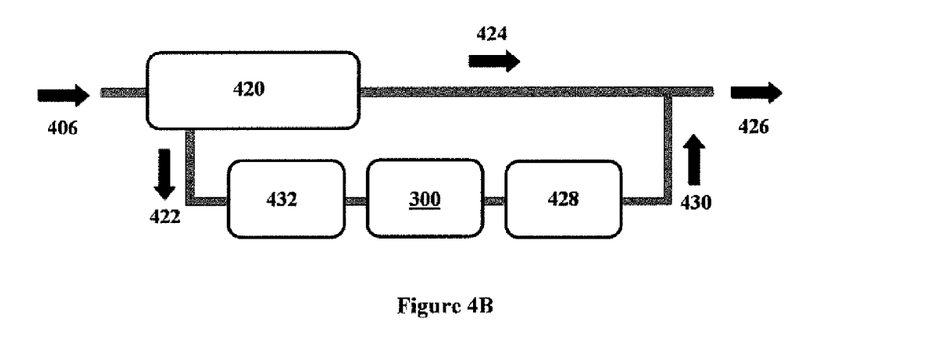
FIG. 4B shows another preferred embodiment of device for enhanced antimicrobial PDT treatment coupled to continuous plasma filtration adsorption therapy, including photosensitizer delivery system.
Figure 5:
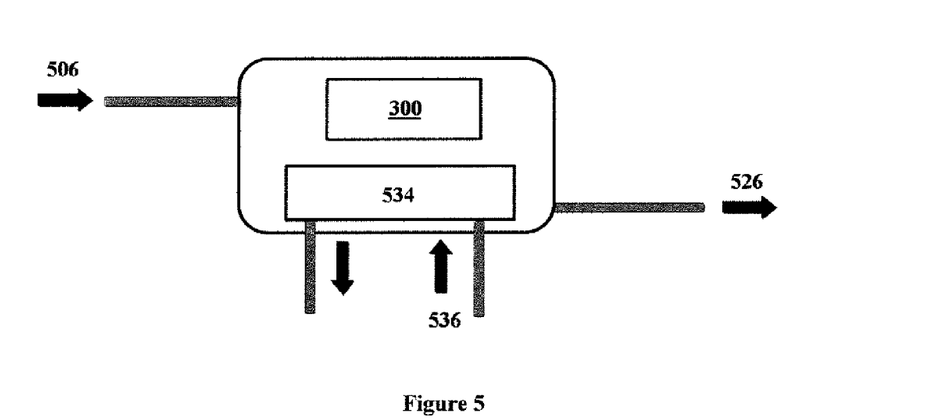
FIG. 5 represents a preferred embodiment showing device for enhanced antimicrobial PDT treatment coupled with continuous veno-venous hemodialysis system.
Figure 6A:
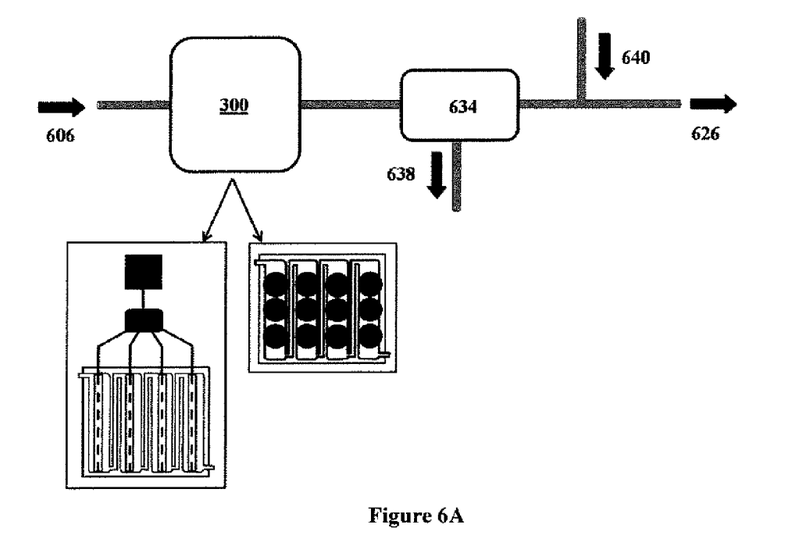
FIG. 6A depicts a preferred embodiment that combines high-volume hemofiltration with antimicrobial PDT device.
Figure 6B:
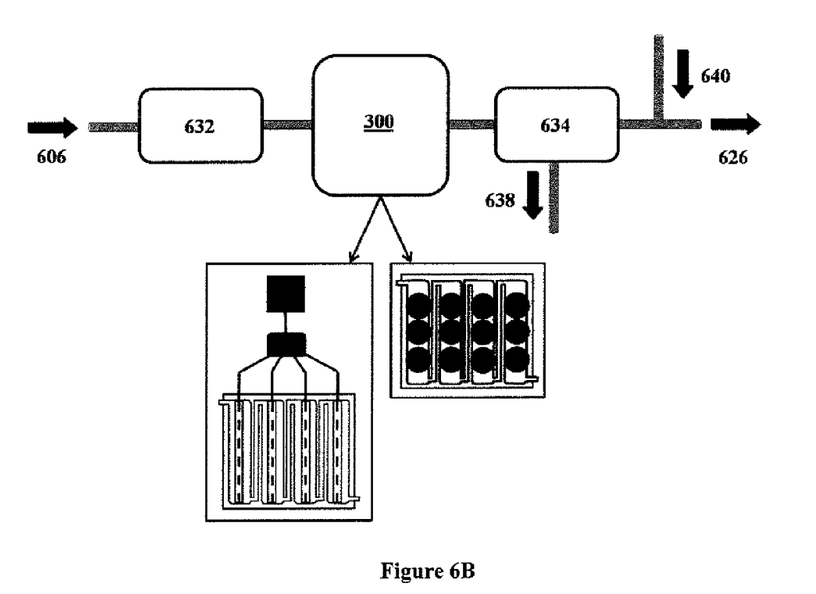
FIG. 6B shows another preferred embodiment combining high-volume hemofiltration, antimicrobial PDT device and photosensitizer delivery system.

To effectively treat sepsis, a systemic inflammatory response syndrome caused by infection, previously cited devices for enhanced antimicrobial PDT treatment are coupled to extracorporeal blood purification techniques. It has been proposed that the sepsis syndrome reflects an imbalance of pro- and anti-inflammatory mediators and it is the abnormal peak levels of such substances that cause pathogenesis. In severe conditions sepsis may progress to multiple organ dysfunction, hypoperfusion, hypotension and eventually death. Pathogenic agents include bacteria, particularly Gram negative bacteria which secrete endotoxins when lysed. This is due to the lipopolysaccharide (LPS) content of the Gram negative cell wall which may trigger septic shock when released into the blood stream, inducing a complex inflammatory cascade of cellular, mediator and cytokine-related events. Thus, it is important to neutralize or remove the LPS released and the pathogenic fragments present after destroying pathogenic agents. The advantageous combination of extracorporeal blood purification techniques with antimicrobial PDT therapy provides a potent therapeutic treatment against sepsis due to the effective removal of inflammatory mediators combined with the killing and removal of a broad spectrum of pathogenic molecules. FIGS. 4-6 present preferred embodiments of the present invention for the treatment of sepsis. FIG. 4A depicts constituting elements of a continuous plasma filtration adsorption therapy coupled to illumination unit/device 300, described before. Contaminated-medium 406 with photosensitizer flows through plasma filter 420. Plasma filter 420 separates plasma 422 from whole blood 424. Whole blood 424 continues flowing and becomes venous return fluid 426. Contaminated plasma 422 with photosensitizer passes through illumination unit/device 300 where infectious bacteria is fully or partially killed, reduced, destroyed and/or eliminated by laser or LED radiation, tuned to the activation wavelength of the selected photosensitizer and emitted intermittently in a preselected pattern. Then, treated contaminated plasma flows through absorbent/filter 428 where substances of different molecular weight are trapped. Depending on its design, absorbent/filter 428 removes dead bacterial cells, pathogenic microorganism fragments, endotoxins, excess or non-activated photosensitizer molecules or any other undesired particle. Treated plasma 430 adds to whole blood 424 and constitutes venous return fluid 426. FIG. 4B shows another preferred embodiment, where contaminated-medium 406 flows through plasma filter 420. Plasma filter 420 separates plasma 422 from whole blood 424. Whole blood 424 continues flowing and becomes venous return fluid 426. Contaminated plasma 422 is guided to photosensitizer delivery system 432 where a photosensitizer or photosensitizer precursor is delivered to contaminated plasma 422. Contaminated plasma 422 combined with photosensitizer flows through illumination unit/device 300 where infectious bacteria is fully or partially killed, reduced, destroyed and/or eliminated by laser or LED radiation, tuned to the activation wavelength of the selected photosensitizer and emitted intermittently in a preselected pattern. Then, treated contaminated plasma flows through absorbent/filter 428 where substances of different molecular weight are trapped such as dead bacterial cells, pathogenic microorganism fragments, endotoxins, excess or non-activated photosensitizer molecules and the like. Treated plasma 430 combines with whole blood 424 and constitutes venous return fluid 426.

In a preferred embodiment, depicted in FIG. 5, antimicrobial PDT device is coupled with continuous veno-venous hemodialysis system. Contaminated-medium 506 with photosensitizer flows through a system comprising illumination unit/device 300 and filter 534. Device 300 allows fully or partially killing, reduction, destruction and/or elimination of infectious bacteria by laser or LED radiation, tuned to the activation wavelength of the selected photosensitizer and intermittent emission in a preselected pattern. Filter 534 provides clearance of different molecular weight substances involving diffusion of molecules across a semi-permeable membrane while dialysate 536 flows in the opposite direction to contaminated-medium 506. Filter 534 has a photosensitizer absorbent to eliminate the excess or non-activated photosensitizer molecules and a section for neutralizing and/or removing endotoxins, pathogenic microorganism fragments, dead cells, pathogenic microorganisms and the like. Treated medium constitutes venous return fluid 526.

FIGS. 6A and B show a preferred embodiment that combines high-volume hemofiltration with antimicrobial PDT device. The embodiment depicted in FIG. 6A shows contaminated-medium 606 with photosensitizer flowing through illumination unit/device 300 where infectious bacteria is fully or partially killed, reduced, destroyed and/or eliminated by laser or LED radiation, tuned to the activation wavelength of the selected photosensitizer and intermittent emission in a preselected pattern. Following the antibacterial PDT treatment, treated medium flows through filter 634, where waste products 638 such as water and substances of large and small molecular weight such as endotoxins, pathogenic microorganism fragments, dead cells, pathogenic microorganisms, excess or non-activated photosensitizer molecules and the like are drained by a positive hydrostatic pressure. Isotonic replacement fluid 640 is added to replace fluid volume and electrolytes. Antibacterial PDT treated medium and isotonic replacement fluid 640 constitutes venous return fluid 626. FIG. 6B shows another embodiment of high-volume hemofiltration combined with antimicrobial PDT device where contaminated-medium 606 is guided to photosensitizer delivery system 632 where a photosensitizer or photosensitizer precursor is delivered to contaminated-medium 606. Contaminated-medium 606 combined with photosensitizer flows through illumination unit/device 300 where infectious bacteria is fully or partially killed, reduced, destroyed and/or eliminated by laser or LED radiation. Radiation is tuned to the activation wavelength of the selected photosensitizer and is emitted intermittently in a preselected pattern. Following the antibacterial PDT treatment, treated medium flows through filter 634, where waste products 638 such as endotoxins, pathogenic microorganism fragments, dead cells, pathogenic microorganisms, excess or non-activated photosensitizer molecules and the like are drained by a positive hydrostatic pressure. Isotonic replacement fluid 640 is added to replace fluid volume and electrolytes. Antibacterial PDT treated medium and isotonic replacement fluid 640 constitutes venous return fluid 626.

In a preferred embodiment a method that enhances PDT activity aiming to kill, reduce and/or destroy undesired body fluid species, such as pathogen microorganisms and deteriorated or malignant cells, in complex body fluids, includes the following steps, 1) mixing a photosensitizer or photosensitizer composition or precursor with the complex body fluid to be treated;

2) after a dwell time, emitting electromagnetic radiation tuned to the activation wavelength of the selected photosensitizer to contaminated complex body fluid mixed with photosensitizer;

3) removing, neutralizing or inactivating endotoxins, pathogenic microorganism fragments, dead cells, pathogenic microorganisms, excess or non-activated photosensitizer molecules and the like; and 4) as necessary, restoring treated complex body fluids to corresponding body regions.

The photosensitizer, photosensitizer composition or photosensitizer precursor may be mixed with the complex body fluid to be treated either inside the living organism, e.g. by administering the photosensitizer intravenously; or outside of said living organism, e.g. in sterile container bags. Preferably, the complex body fluid mixed with the photosensitizer is treated and/or mixed while inside specific channels as depicted in previous device embodiments.

Electromagnetic radiation is preferably emitted intermittently in a preselected pattern with a laser or LED source. During irradiation undesired body fluid species are destroyed, while breaks between irradiations allow the establishment of new equilibrium and photosensitizer replenishment at/near undesired body fluid species.

Before restoring treated complex body fluids to corresponding patient's body, the photosensitizer should have been completely or partially eliminated or inactivated. Removal or inactivation of excess or non-activated photosensitizer present in treated blood may be done by adjusting the electromagnetic radiation pattern of delivery, delivered electromagnetic radiation many times, by using a photosensitizer-absorber or by any other means.

In order to neutralize, inactivate and/or remove endotoxins (e.g. LPS), pathogenic microorganism fragments and dead cells as stated in step 3, many approaches may be used. Preferably, neutralization, inactivation and/or removal are performed with the aid of a filter. Additionally, other known-in-the-art methods employed to neutralize and/or inactivate endotoxins and pathogenic microorganism fragments may be used, including the administration of antibodies, peptides, members of the Scavenger Receptor Cysteine-Rich superfamily, and others. After neutralizing and/or inactivating endotoxins and pathogenic microorganism fragments, they can also be removed with the aid of a filter. In any case, the objective is to use a concomitant therapy which neutralizes or inactivates endotoxins and pathogenic fragments in order to reduce the inflammatory processes that may be developed in case these endotoxins and pathogenic fragments reach the living organism's blood stream.

In another preferred embodiment a method that enhances PDT activity aiming to kill, reduce and/or destroy undesired body fluid species, such as pathogen microorganisms and deteriorated or malignant cells, in complex body fluids, includes the following steps, 1) extracting contaminated body fluid from a living organism and guiding it through a specific tube as depicted in previous device embodiments;

2) administering a photosensitizer or a photosensitizer composition or precursor to the contaminated medium, such as body fluid or to an extract of said body fluid;

3) emitting laser or LED radiation tuned to the activation wavelength of the selected photosensitizer intermittently in a preselected pattern while contaminated medium flows inside tube;

4) restoring treated medium to corresponding body regions.

In another preferred embodiment, previously described methods enhance antimicrobial PDT activity due to their ability to kill, reduce and/or destroy microbes, such as Gram (−) and Gram (+) bacteria.

During irradiation bacteria is destroyed, while breaks between irradiations allow the establishment of new equilibrium and photosensitizer replenishment at/near bacterial surfaces.

When preferably the photosensitizer composition comprises a dye known as Safranin O, the preferred laser radiation wavelength is in the range of 500-580 nm, preferably around 530 nm. Nevertheless the use of other photosensitizers and photosensitizers' compositions are not limited thereto and the preferred radiation wavelength will be dependent on the absorption spectrum of the selected photosensitizer.

Figure 7:
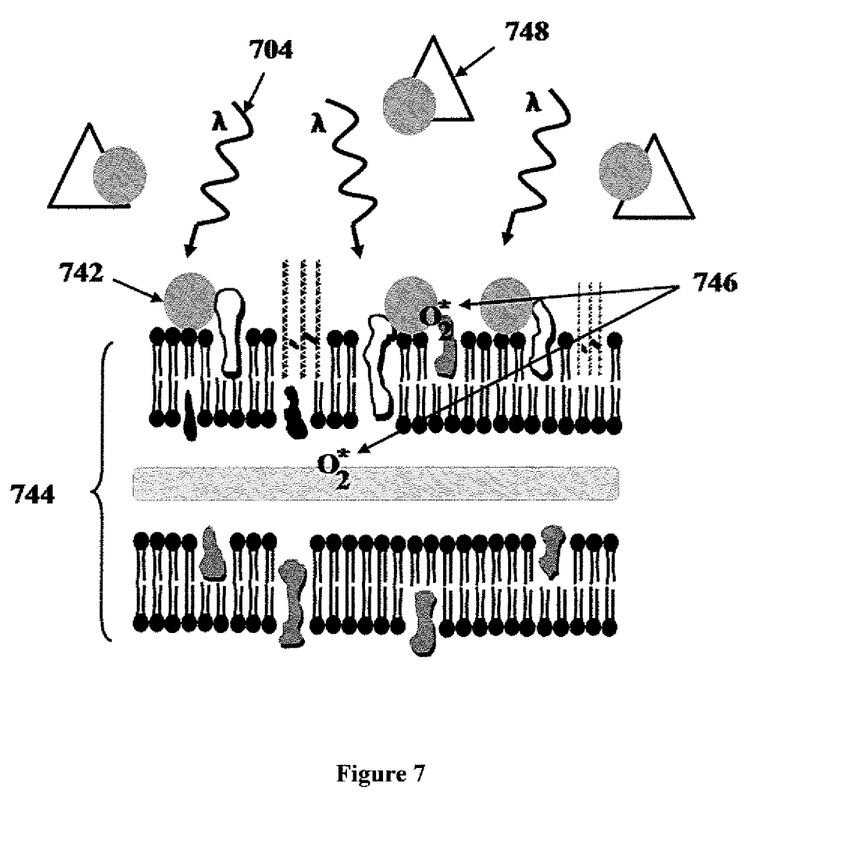
FIG. 7 shows resistant Gram (−) double layer and irradiation effect in bacteria when applying intermittent laser radiation.

In preferred embodiments, the method that enhances antimicrobial PDT activity against microbes such as Gram (−) and Gram (+) bacteria in complex body fluids, comprises intermittent radiation delivery. Pulse width depends on diverse parameters affecting the PDT treatment such as contamination degree, bacteria-contaminated fluid flow, photosensitizer doses, and other electromagnetic radiation parameters including power, energy and time. Laser radiation of appropriate wavelength 704 excites photosensitizer molecules 742 at/near Gram (−) bacteria double-layer membrane 744 to the excited singlet state. This excited singlet state lowers its energy becoming a triplet state which then reacts by two known photoprocesses that require oxygen, either producing radical ions that can then react with oxygen to produce cytotoxic species or producing excited-state singlet oxygen 746 that diffuse through Gram (−) bacteria double-layer membrane 744 to oxidize biological molecules and lead to cytotoxicity. A portion of photosensitizer molecules 742 that were captured by serum protein molecules 748, such as albumin, is largely left unbleached, due to the relative lack of oxygen molecules at albumin sites. Thus, during the off period before the following irradiation, photosensitizer molecules 742 that were captured by serum protein molecules 748 are released and a new equilibrium is established, replenishing photosensitizers at/near the Gram (−) bacteria double layer membrane 744. Many cycles of illumination can be performed to effectively kill, destroy and/or inactivate bacteria even in complex body fluids.

The present invention is further illustrated by the following examples, but is not limited thereby.

Example 1

In a separate test a composition comprising Safranin O was added to calf serum (100% serum) solution containing Staphylococcus aureus (Gram (±) bacterium), which is a common component of the micro flora of wounds, resulting in a final concentration of 20 $\mu$M Safranin O in 99% calf serum. Irradiation was delivered in a flow system corresponding to FIG. 3 B via a light fiber from a laser, Ceralas G2 (Biolitec AG, Germany) operating at 532 nm and using a fluence rate of 30 mW/cm$^2$. After three passages through this flow system using a flow rate of 10 ml/min and continuous irradiation the percentage of killing of bacteria observed was about 99.9%.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method for enhanced photodynamic therapy aiming to reduce, kill or eliminate undesired body fluid species found in diluted or undiluted serum or solutions containing blood or blood compounds from a living organism, comprising the steps of:
   a) mixing a photosensitizer with a complex body fluid comprising whole blood;
   b) waiting a preselected dwell time to permit association of said photosensitizer and undesired body fluid species of the complex body fluid;
   c) passing the complex body fluid associated with the photosensitizer through a filter and separating plasma from the whole blood;
   d) guiding said separated plasma through an array of cylindrical channels containing LED-panels at least three times at a flow rate of 10 ml/min;
   e) irradiating said separated plasma with an electromagnetic radiation source tuned to an activation wavelength of the selected photosensitizer;
   f) processing the irradiated plasma to remove, neutralize or inactivate endotoxins, pathogenic microorganism fragments, dead cells, pathogenic microorganisms, excess or non-activated photosensitizer molecules;
   g) combining the processed plasma with the whole blood from which the plasma was separated in step c to form a venous return fluid; and
   h) returning said venous return fluid to its corresponding body regions of the living organism.

2. The method according to claim 1, wherein said photosensitizer is selected from the group consisting of a photosensitizer, a photosensitizer composition and a photosensitizer precursor.

3. The method according to claim 2, wherein said photosensitizer is Safranin O.

4. The method according to claim 1, wherein said irradiating step is characterized by application of pulsed electromagnetic radiation.

5. The method according to claim 4, wherein a pattern of said application of pulsed electromagnetic radiation has a pulse width selected according to contamination degree, bacteria-contaminated fluid flow, photosensitizer dose, electromagnetic radiation power, electromagnetic radiation energy, time and combinations of them.

6. The method according to claim 1, wherein said undesired body fluid species refers to pathogenic microorganisms, including bacteria and viruses.

7. The method according to claim 6, wherein said bacteria includes Gram (+) and Gram (−) bacteria.

8. The method according to claim 1, wherein said undesired body fluid species refers to deteriorated or malignant cells, such as cancer cells.

9. The method according to claim 1, wherein said method further comprises the step of removing or inactivating excess or non-activated photosensitizer present in the separated plasma or whole blood by adjusting the electromagnetic radiation pattern of delivery, delivering electromagnetic radiation many times, using a photosensitizer-absorber or by any other means.

10. The method according to claim 1, wherein said photosensitizer is mixed with the complex body fluid inside the living organism or outside of said living organism.

\* \* \* \* \*